United States Patent [19]

Ott

[11] Plant 4,310

[45] Sep. 26, 1978

[54] POINSETTIA

[76] Inventor: Cleveland Ott, 677 Grater Ave., Graterford, Pa. 19426

[21] Appl. No.: 732,369

[22] Filed: Oct. 14, 1976

[51] Int. Cl.[2] ..... A01H 5/00

[52] U.S. Cl. ..... Plt./86

[58] Field of Search ..... Plt./86

[56] References Cited

U.S. PATENT DOCUMENTS

| | | | |
|---|---|---|---|
| P.P. 2,962 | 1/1970 | Hegg | Plt./86 |
| P.P. 3,160 | 5/1972 | Ecke | Plt./86 |
| P.P. 3,392 | 8/1973 | Ecke | Plt./86 |
| P.P. 3,764 | 8/1975 | Hegg | Plt./86 |

*Primary Examiner*—Robert E. Bagwill

*Assistant Examiner*—James R. Feyrer

*Attorney, Agent, or Firm*—Paul & Paul

[57] ABSTRACT

A new and distinct variety of poinsettia is characterized by a flower having generally the same characteristics as its parent, Annette Hegg Supreme (U.S. Plant Pat. No. 3,392) but the new variety is a brighter darker red and under normal growing conditions the bracts are between 10 percent and 40 percent wider with less open space between bracts. The new plant is 10–20 percent shorter than its parent and is more compact. The new plant blooms 3–5 days earlier than its parent. The new variety is a self branching plant. When pinched, the sprouts finish more uniformly than the parent. Leaf and bract retentions are equal to those of the parent.

1 Drawing Figure

ORIGIN OF THE VARIETY

The new variety of poinsettia was discovered by applicant as a sport in a bed of Annette Hegg Supreme poinsettias (U.S. Plant Pat. No. 3,392) in applicant's greenhouse near Graterford, Pa. This discovery was made in December, 1974 but none of the new variety was sold, or offered for sale, until the following season, December, 1975.

ASEXUAL REPRODUCTION OF THE VARIETY

Following applicant's discovery, applicant asexually reproduced the new and distinct variety in his greenhouse by the rooting of cuttings from the new sport. The asexually reproduced poinsettias have uniformly new and distinct characteristics.

SUMMARY OF THE VARIETY

The new and distinct variety of poinsettias is characterized by the following features:

(1) The color is bright red but a darker red than the parent, Annette Hegg Supreme; the closest designations of the color of the new variety of poinsettia on the Royal Horticultural Society (R.H.S.) color chart are 44-A and 45-B. On the British Colour Council (B.C.C.) Dictionary of Colour Standards the closest designation is "Post Office Red BCC209". On Wilson's Horticultural Color Chart, the closest designation is Blood Red No. 820.

(2) The bracts are between 10 and 40% wider than the parent, Annette Hegg Supreme, and there is less open space between bracts.

(3) The new plant is approximately 10–20 percent shorter than its parent and is more compact.

(4) The plant grows more uniformly than does the parent, Annette Hegg Supreme.

(5) When pinched, the sprouts finish more uniformly than do the sprouts of the parent, Annette Hegg Supreme.

(6) Leaf and bract retentions are equal to those of the parent.

BRIEF DESCRIPTION OF THE DRAWING

The drawing comprises two different photographic reproductions in color of the new and distinct poinsettia of this application. One photograph is a reduced perspective view of the potted new poinsettia plant. The other photograph is a reduced close-up view of one of the groups of bracts.

DETAILED DESCRIPTION OF THE VARIETY

The new and distinct variety of poinsettia of this application was asexually reproduced from a sport of the parent, Annette Hegg Supreme (U.S. Plant Pat. No. 3,392). The parent, Annette Hegg Supreme, is a sport of Annette Hegg (U.S. Plant Pat. No. 2,962). The new poinsettia has generally the same characteristics as its parent, Annette Hegg Supreme, but the color of the new variety is a brighter darker red than the Annette Hegg Supreme.

A comparison of the color of the bracts of the new variety of poinsettia with those of its parent (U.S. Plant Pat. No. 3,392), its grandparent (U.S. Plant Pat. No. 2,962), and other related sports, on Wilson's Horticultural Color Chart are as follows:

Ott Sport (U.S. Plant patent application Ser. No. 732,369) — Blood Red — #820

Annette Hegg (U.S. Plant Pat. No. 2,962) — Currant Red — #821/3

Annette Hegg Supreme (U.S. Plant Pat. No. 3,392) — Blood Red — #820/3

Dark Red Annette Hegg (U.S. Plant Pat. No. 3,160) — Currant Red — #821/2

Annette Hegg Lady (U.S. Plant Pat. No. 3,764) — Currant Red — #821/2

The bracts of the new variety are wider from 10 to 40% than bracts of the parent Annette Hegg Supreme so that there is less open space between bracts.

The new plant is 10–20 percent shorter than its parent and is more compact.

The new plant is a self branching plant. When pinched, the sprouts finish more uniformly than do the sprouts of the Annette Hegg Supreme. The plant grows more uniformly than the Annette Hegg Supreme.

The plant has very good leaf and bract retention. The plants retain their beauty for many weeks.

The new plant blooms 3 to 5 days earlier than its parent, Annette Hegg Supreme. It also blooms 3 to 5 days earlier than its grandparent, Annette Hegg (2,962), and its sport Dark Red Annette Hegg (3,160).

What is claimed is:

1. A new and distinct variety of poinsettia plant, substantially as herein illustrated and described, characterized particularly as to novelty by a color which is bright red but a darker red than its parent, Annette Hegg Supreme (U.S. Plant Pat. No. 3,392), its grandparent, Annette Hegg (U.S. Plant Pat. No. 2,962), and related sports which have evolved directly or indirectly from said grandparent, bracts which are between 10 and 40% wider than in the parent Annette Hegg Supreme, thereby providing less open space between bracts, a plant which is approximately 10–20 percent shorter and is more compact than its parent, Annette Hegg Supreme, its grandparent, Annette Hegg, and sports thereof, a plant which grows more uniformly than does the parent, Annette Hegg Supreme, a plant which blooms 3–5 days earlier than its parent and its grandparent, and a plant which has good leaf and bract retentions equal to that of the parent.

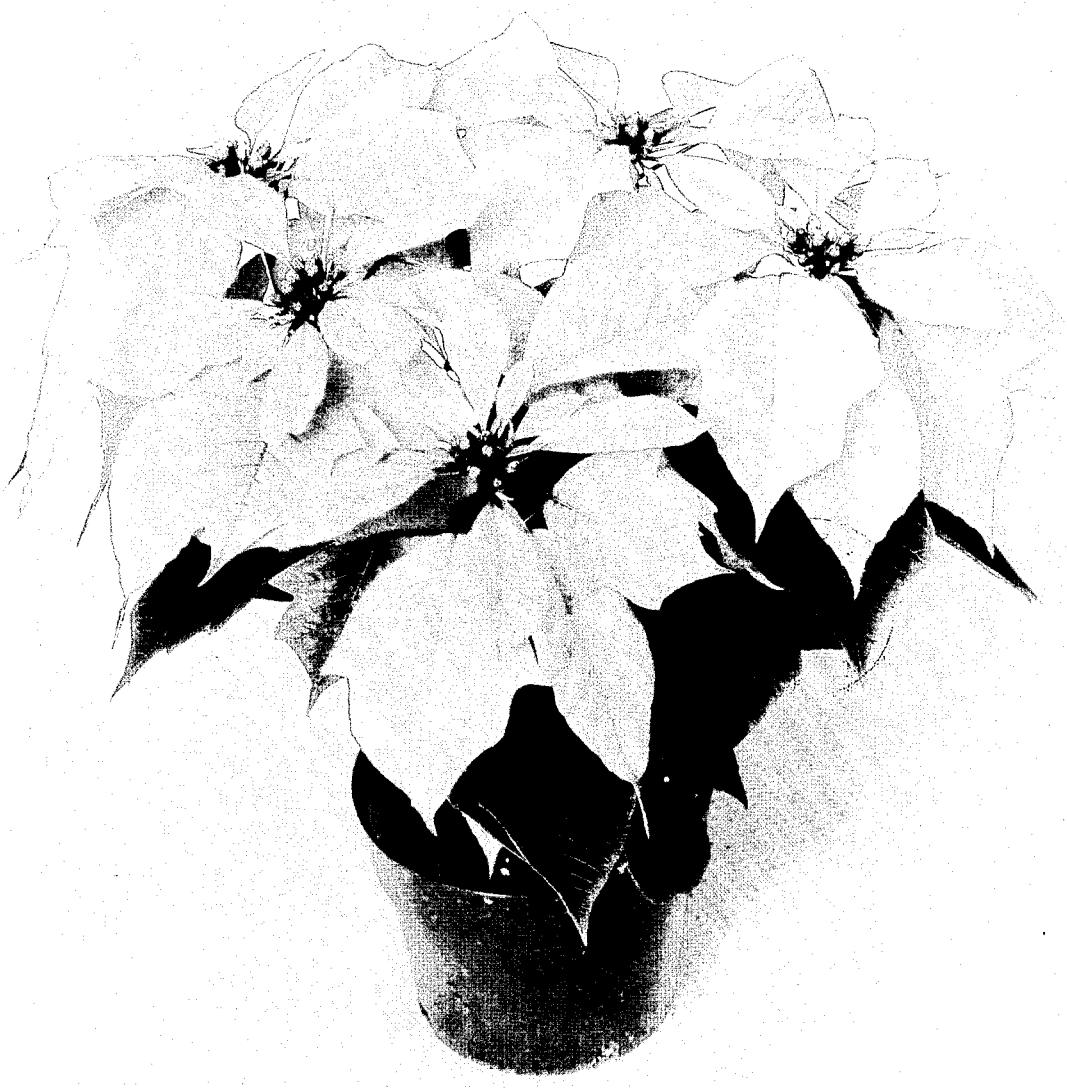

* * * * *